United States Patent [19]
Suyama

[11] Patent Number: 5,211,713
[45] Date of Patent: May 18, 1993

[54] TEMPERATURE CONTROL METHOD WITH SIMULTANEOUS HEATING AND COOLING NEAR THE SET-POINT

[75] Inventor: Katsumasa Suyama, Hirakata, Japan

[73] Assignee: Tabai Espec Corp., Osaki, Japan

[21] Appl. No.: 737,744

[22] Filed: Jul. 30, 1991

[30] Foreign Application Priority Data

Nov. 30, 1990 [JP] Japan ................................ 2-340983

[51] Int. Cl.⁵ ..................... F25B 29/00; F28F 27/00
[52] U.S. Cl. ................................. 165/2; 165/26; 165/27; 165/30; 165/48.1; 165/63; 165/64; 62/505
[58] Field of Search ............ 165/30, 61, 63, 64, 165/27, 26, 48.1, 2; 62/505

[56] References Cited

U.S. PATENT DOCUMENTS

| | | | |
|---|---|---|---|
| Re. 31,903 | 6/1985 | Faillace | 165/30 |
| 2,801,799 | 8/1957 | McColloch | 236/46 F |
| 3,229,754 | 1/1966 | Hoag | 165/30 |
| 3,637,006 | 1/1972 | Decker | 165/30 |
| 3,692,100 | 9/1972 | Gallagher, Jr. | 165/64 |
| 4,548,259 | 10/1985 | Tezuka et al. | 165/63 |
| 4,784,213 | 11/1988 | Eager et al. | 165/64 |
| 4,984,628 | 1/1991 | Uchida et al. | 165/63 |

FOREIGN PATENT DOCUMENTS

47-29265  1/1972  Japan.
2056694  3/1981  United Kingdom .................. 165/61

OTHER PUBLICATIONS

"An Application Note" by Control Systems. (No date).

*Primary Examiner*—John K. Ford
*Attorney, Agent, or Firm*—Armstrong, Westerman, Hattori, McLeland & Naughton

[57] ABSTRACT

A temperature control method for controlling a temperature in a chamber comprises the steps of: providing heating means which can select large and small heating powers for heating the chamber and refrigerating means for cooling the chamber; detecting a process temperature in the chamber; operating the heating means with a small heating power for attaining an intended set value when a detected temperature is equal to or higher than a lower tolerable deviation value, and operating the heating means with a large heating power when the detected temperature is lower than the lower tolerable deviation value; and operating the refrigerating means when the detected temperature is higher than an upper tolerable deviation value.

4 Claims, 8 Drawing Sheets

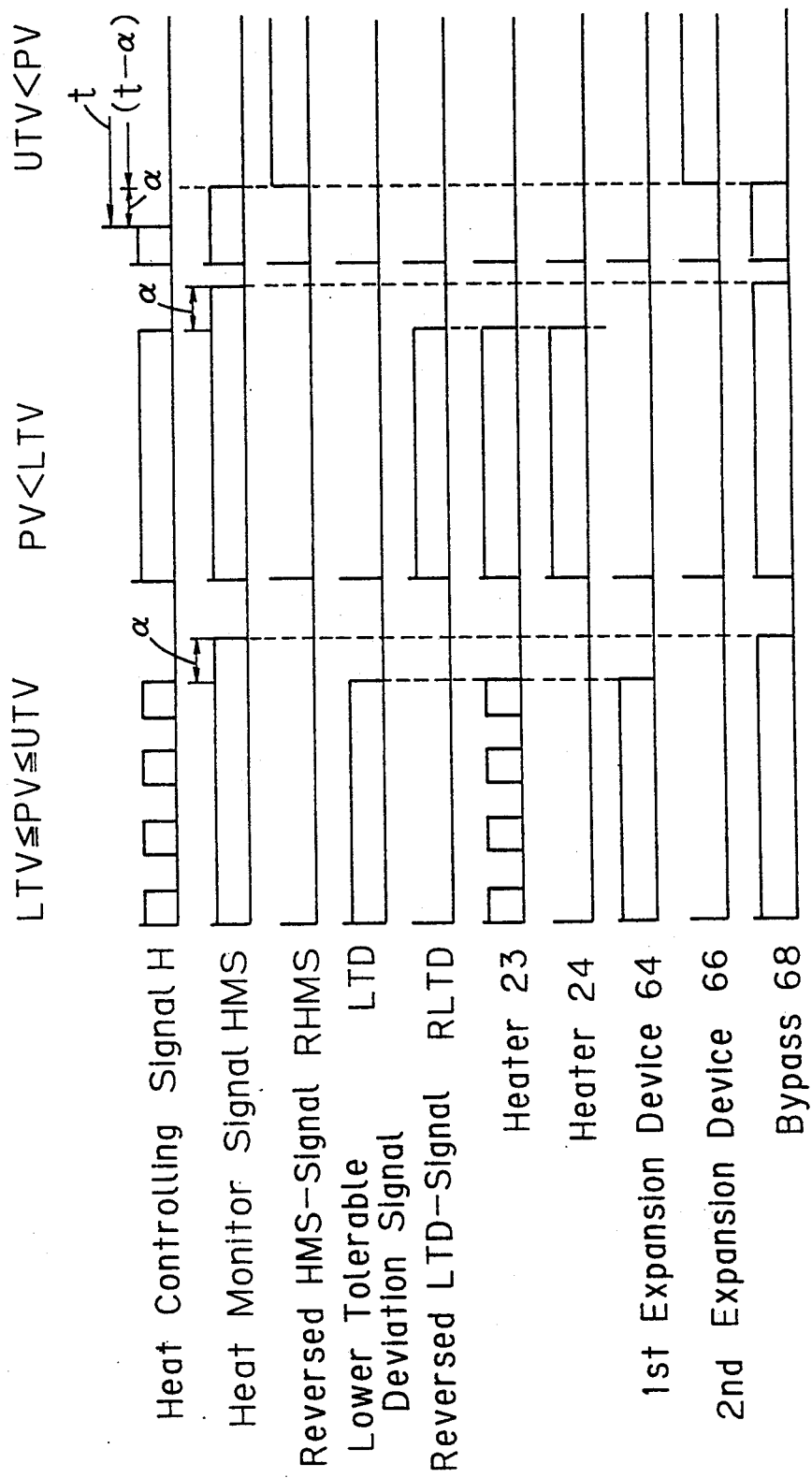

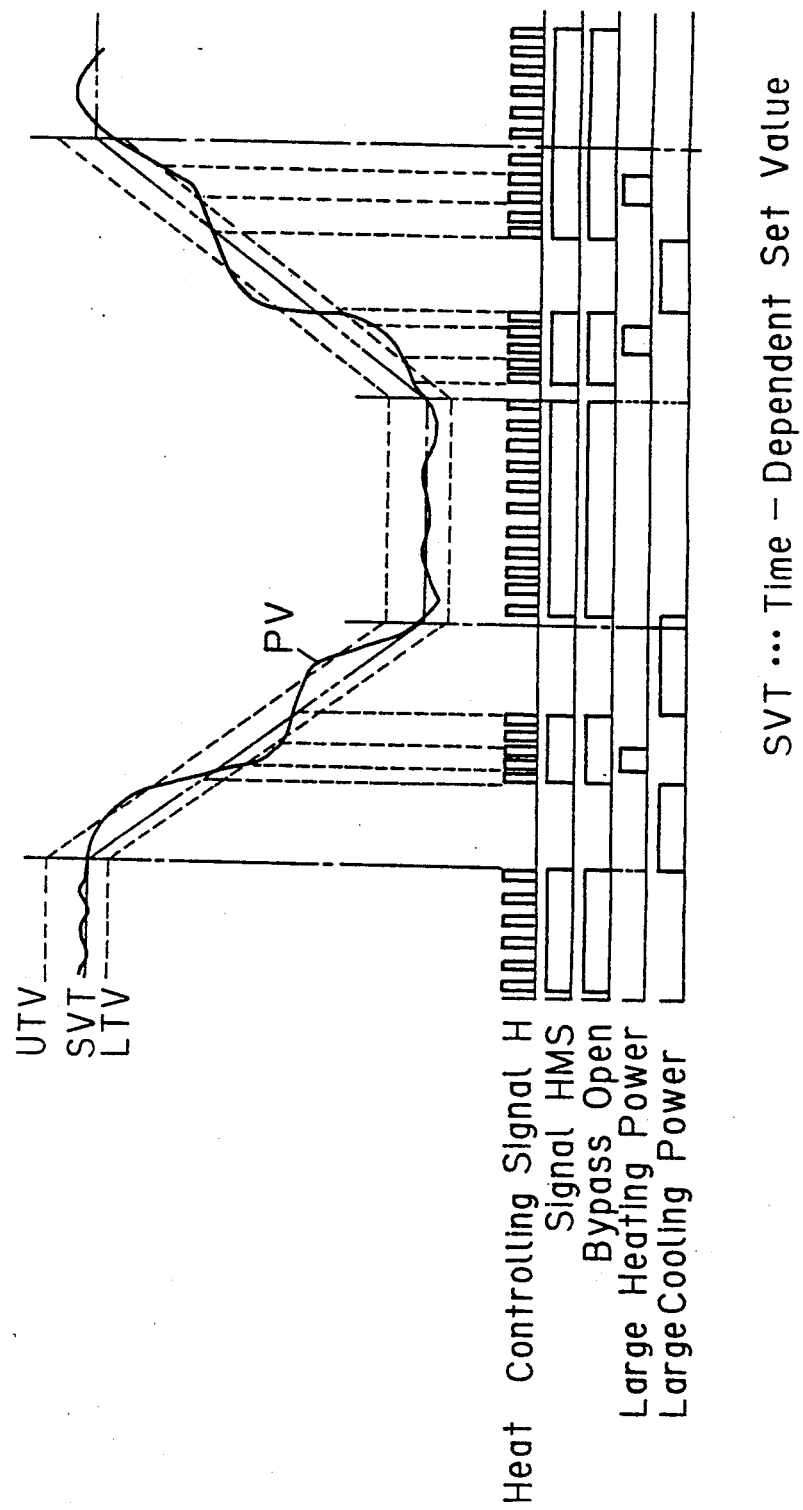

TEMPERATURE CONTROL METHOD WITH SIMULTANEOUS HEATING AND COOLING NEAR THE SET-POINT

BACKGROUND OF THE INVENTION

1. Field of the Invention

The present invention relates to a method for controlling temperatures in chambers, for example, of environmental testing equipments such as temperature tanks in which predetermined temperatures are to be maintained and temperature/humidity tanks in which predetermined temperatures and humidities are to be maintained. Such chambers are used for testing high and lower temperature resistances, moisture resistance and other characteristics of various electric and electronic products and parts thereof as well as various kinds of material in predetermined temperatures and/or humidities, and are also used for burn-in, screening and others.

2. Description of the Related Art

Temperature control in chambers, e.g., of the environmental testing equipments has been carried out as follows.

Heating means for heating the chamber and cooling means having a constant cooling power for cooling the chamber are used, and an operation of only the heating means is controlled by heat controlling signals which are formed by a temperature controller as a result of PID operation dependent on process temperatures in the chamber, so that the temperature control is performed by balancing a heating rate or power of the heating means and a cooling rate or power of the cooling means.

In the prior art, the powers of the heating means and the cooling means are restricted so as to balance the heating power and the cooling power for the temperature control, and thus cannot exceed the powers required for attaining the balance. Consequently, it is impossible to rapidly increase the chamber temperature which has lowered to a value lower than a lower tolerable deviation value predetermined with respect to an intended set value of the temperature, and it is also impossible to rapidly lower the chamber temperature even when the chamber temperature is higher than an upper tolerable deviation value predetermined with respect to the set value.

It powers larger than the restricted heating and cooling powers were applied to the means in order to reduce a period of time required for raising and lowering the temperature, the temperature control would become extremely instable, which impedes a practical use.

Further, in the temperature controller of the prior art, a large cooling power may be required for rapid discharge of heat when the chamber temperature exceeds the upper tolerable deviation value, for example, due to the heat from an article located in the chamber. However, such signals are not available that activate a cooling source or increase the cooling power thereof in accordance with variation of conditions in the chamber caused by the heating. Therefore, there is a disadvantage that the cooling source can be activated and adjusted only by a manual operation, even if the cooling source having a large capacity is employed.

As a method for overcoming the above disadvantage, it may be contemplated that the rapid increase or decrease of the temperature can be achieved by temperature control means which can supply cooling signals having the PID operation outputs which are symmetrical to the heat controlling signals with respect to a line. In this method, however, the chamber temperature cannot accurately follow the set temperature having a given constant value or a variable value dependent on a time, as can be done in the case previously described, in which the heating power and the cooling power are balanced with each other. Particularly, if the time-dependent set value is to be followed by the chamber temperature, the temperature control characteristics cannot be practically used, for example, in the environmental testing equipments.

Accordingly, it is a first object of the invention to provide a temperature control method for controlling the temperature in the chamber to a constant set value, in which the chamber temperature can be rapidly raised when a current temperature in the chamber deviates from the set value and lowers to or below the lower tolerable deviation value, and the chamber temperature can be rapidly lowered when the chamber temperature is raised to or above the upper tolerable deviation value, for example, due to the heat supplied from an article in the chamber, whereby the chamber temperature can be stably maintained at or near the set value.

A second object of the invention is to provide a temperature control method for controlling the temperature in the chamber to an intended time-dependent set value which varies in accordance with a time, in which the chamber temperature can sufficiently follow the time-dependent set value.

SUMMARY OF THE INVENTION

In accordance with the first object of the invention, there is provided a temperature control method (first method) for controlling a temperature in a chamber to an intended constant set value, the method comprising the steps of: providing heating means which can select large and small heating powers for heating the chamber and refrigerating means for cooling the chamber; detecting a current temperature in the chamber; operating the heating means with a low heating power for attaining the set value when a detected temperature is equal to or higher than a lower tolerable deviation value predetermined with respect to the set value of the chamber temperature, and operating the heating means with a large heating power when the detected temperature is lower than the lower tolerable deviation value; and operating the refrigerating means when the detected temperature is higher than an upper tolerable deviation value predetermined with respect to the set value of the chamber temperature (see FIG. 1).

This first method is suitable to a case in which the set value is considerably higher than an environmental temperature around the chamber and the cooling power is not basically required.

In this first method, the heating means may include a heater having a small heating power and a heater having a large heating power, which are selectively used. Alternatively, a first and second heater method may be employed, in which the heating means includes first and second heaters so that a small heating power may be obtained by the first heater and the large heating power may be obtained by both the first and second heaters.

Further, a heat monitor method may be employed in order to operate the refrigerating means when the detected temperature is higher than the upper tolerable deviation value. In this heat monitor method, operation control means for the heating means is designed to supply heat controlling signals for operating the heating means at least during the operation of the heating means with the small heating power, and, when a time interval between adjacent heat controlling signals is larger than a predetermined value, the refrigerating means is operated for a period from elapsing of a period corresponding to the predetermined value to elapsing of the time interval between adjacent heat controlling signals.

Further, in accordance with the first object of the invention, there is provided a temperature control method (second method) for controlling a temperature in a chamber to an intended constant set value, the method comprising the steps of: providing heating means which can select large and small heating powers for heating the chamber and refrigerating means which can select large and small cooling powers for cooling the chamber; detecting a current temperature in the chamber; operating the heating means with a small heating power for attaining the set value when a detected temperature is equal to or higher than a lower tolerable deviation value predetermined with respect to the set value of the chamber temperature, and operating the heating means with a large heating power when the detected temperature is lower than the lower tolerable deviation value; and operating the refrigerating means with a small cooling power when the detected temperature is equal to or higher than the lower tolerable deviation value and is equal to or lower than the upper tolerable deviation value, and operating the refrigerating means with a large cooling power when the detected temperature is higher than the upper tolerable deviation value (see FIG. 2).

This second method is suitable to a case in which the set value is relatively low and the cooling capacity is essentially or preferably required for the temperature control.

Also in this second method, a first and second heater method may be employed, in which the heating means includes first and second heaters so that a small heating power may be obtained by the first heater and the large heating power may be obtained by both the first and second heaters.

Further, the refrigerating means may include a refrigerator having a small refrigerating capacity and a refrigerator having a large refrigerating capacity, which are selectively used. Alternatively, a first and second expansion system method may be employed, in which the refrigerating means includes first and second expansion means so that the small cooling power may be obtained by opening the first expansion means and closing the second expansion means and the large cooling power may be obtained by opening both the first and second expansion means.

In this case, the refrigerating means may be of a bypass type in which a closable bypass connecting a condenser and a compressor of the refrigerating means together is provided. The compressor is continuously operated during the temperature control. The first and second expansion means are closed and the bypass is opened when the detected temperature is lower than the lower tolerable deviation value. The small cooling power is obtained by opening the first expansion means while maintaining the bypass open. The large cooling power is obtained by opening the first and second expansion means and closing the bypass (see FIG. 3).

A heat monitor method may be employed in order to perform the operation with the large cooling power when the detected temperature is higher than the upper tolerable deviation value. In this heat monitor method, operation control means for the heating means is designed to supply heat controlling signals for operating the heating means at least during the operation of the heating means with the small heating power, and, when a time interval between adjacent heat controlling signals is larger than a predetermined value, the operation with the large cooling power is performed for a period from elapsing of a period corresponding to the predetermined value to elapsing of the time interval between adjacent heat controlling signals.

Further, in accordance with the second object of the invention, there is provided a temperature control method (third method) for controlling a temperature in a chamber to an intended time-dependent set value which varies in accordance with the time, the method comprising the steps of: providing heating means which can select large and small heating powers for heating the chamber and refrigerating means which can select large and small cooling powers for cooling the chamber; detecting a current temperature in the chamber; operating the heating means with a small heating power for attaining the time-dependent set value when a detected temperature is equal to or higher than a lower tolerable deviation value predetermined with respect to the time-dependent set value of the chamber temperature, and operating the heating means with a large heating power when the detected temperature is lower than the lower tolerable deviation value; and, with respect to the operation of the refrigerating means, supplying heat controlling signals by operation control means for the heating means for operating the heating means at least during the operation of the heating means with the small heating power, operating the refrigerating means with at least the small cooling power when the detected temperature is equal to or higher than the lower tolerable deviation value, and operating the refrigerating means with the large cooling power, when a time interval between adjacent heat controlling signals is larger than a predetermined value, for a period from elapsing of a period corresponding to the predetermined value to elapsing of the time interval between adjacent heat controlling signals.

Also in this third method, a first and second heater method may be employed, in which the heating means includes first and second heaters so that a small heating power may be obtained by the first heater and the large heating power may be obtained by both the first and second heaters.

Further, a first and second expansion system method may be employed, in which the refrigerating means includes first and second expansion means so that the small cooling power may be obtained by opening the first expansion means and closing the second expansion means and the large cooling power may be obtained by opening both the first and second expansion means.

The refrigerating means may be of a bypass type, in which a closable bypass for connecting a condenser and a compressor of the refrigerating means together is provided. The compressor is continuously operated during the temperature control. The first and second expansion means are closed and the bypass is opened when the detected temperature is lower than the lower tolerable deviation value. The small cooling power is obtained by opening the first expansion means while maintaining the bypass open. The large cooling power is obtained by opening the first and second expansion means and closing the bypass.

In the first method according to the invention, as understood from FIG. 1, when the process temperature (detected current temperature) PV in the chamber is equal to or higher than the lower tolerable deviation value LTV which is predetermined with respect to the constant set value SV, the heating means is controlled to operate with the small heating power toward the set value SV. When the process temperature PV is lower than the lower tolerable deviation value LTV, the heating means is operated with the large heating power to rapidly increase the process temperature PV. In the first method, if the first and second heater method is employed, the operation with the small heating power is achieved by the operation of the first heater, and the operation with the large heating power is achieved by the operations of both the first and second heaters.

The refrigerating means is operated when the process temperature PV is higher than the upper tolerable deviation value UTV, whereby the process temperature PV is rapidly lowered.

In the first method, if the heat monitor method is employed for determining the timings for the operation of the refrigerating means, the operation control means for the heating means supplies the heat controlling signals at least during the operation with the small heating power. When the time interval between the adjacent heat controlling signals, which increases in accordance with the increase of the chamber temperature, exceeds the predetermined value (e.g. α sec.), it is determined that the process temperature PV is higher than the upper tolerable deviation value UTV, and the refrigerating means is operated for a period from elapsing of a period corresponding to the predetermined value to elapsing of the time interval between adjacent heat controlling signals.

According to the second method of the invention, as understood from FIG. 2, when the process temperature PV is equal to or higher than the lower tolerable deviation value LTV, the heating means is controlled to operate with the small heating power to attain the set value SV. When the process temperature PV is lower than the lower tolerable deviation value LTV, the heating means is operated with the large heating power to rapidly increase the process temperature (current temperature) PV. If this second method employs the first and second heater method, the operation with the small power is achieved by the operation of the first heater, and the operation with the large heating power is achieved by both the first and second heaters.

The refrigerating means is operated with the small cooling power when the process temperature PV is equal to or higher than the lower tolerable deviation value LTV and is equal to or lower than the upper tolerable deviation value UTV. When it is higher than the upper tolerable deviation value UTV, the operation with the large cooling power is performed to rapidly lower the process temperature PV. If the first and second expansion system method is employed, the operation with the small cooling power is achieved by opening the first expansion means and closing the second expansion means, and the operation with the large cooling power is achieved by opening both the first and second expansion means.

If the bypass method is employed, as understood from FIG. 3, the compressor of the refrigerating means is continuously operated during the control of the temperature. If the process temperature PV is lower than the lower tolerable deviation value LTV, the bypass is opened, and the first and second expansion means are closed. If the process temperature PV is equal to or higher than the lower tolerable deviation value LTV and is equal to or lower than the upper tolerable deviation value UTV, the bypass is opened, the first expansion means is opened and the second expansion means is closed. If the process temperature PV is higher than the upper tolerable deviation value UTV, the bypass is closed, and both the first and second expansion means are opened.

In this second method, if the heat monitor method is employed for determining the timings for the operation of the refrigerating means with the large cooling power, the operation control means for the heating means supplies the heat controlling signals at least during the operation with the small heating power. When the time interval between the adjacent heat controlling signals, which increases in accordance with the increase of the chamber temperature, exceeds the predetermined value (e.g. α sec.), it is determined that the process temperature PV is higher than the upper tolerable deviation value UTV, and the operation with the large cooling power is performed for a period from elapsing of a period corresponding to the predetermined value to elapsing of the time interval between adjacent heat controlling signals.

According to the third method of the invention, when the process temperature PV is equal to or higher than the lower tolerable deviation value LTV, the heating means is controlled to operate with the small heating power to attain the time-dependent set value. When the process temperature PV is lower than the lower tolerable deviation value LTV, the heating means is operated with the large heating power to rapidly increase the process temperature PV. If this third method employs the first and second heater method, the operation with the small power is achieved by the operation of the first heater, and the operation with the large heating power is achieved by both the first and second heaters.

The refrigerating means is operated with the small cooling power at least when the process temperature PV is equal to or higher than the lower tolerable deviation value LTV and is equal to or lower than the upper tolerable deviation value UTV. At least during the operation with the small heating power, the operation control means for the heating means supplies the heat controlling signals. When the time interval between the adjacent heat controlling signals, which increases in accordance with the increase of the chamber temperature, exceeds the predetermined value, it is determined that the process temperature PV is higher than the upper tolerable deviation value UTV, and the operation with the large cooling power is performed for a period from elapsing of a period corresponding to the predetermined value to elapsing of the time interval.

If the first and second expansion system method is employed in the third method, the operation with the small cooling power is achieved by opening the first expansion means and closing the second expansion means, and the operation with the large cooling power is achieved by opening both the first and second expansion means.

If the bypass method is employed, the compressor of the refrigerating means is continuously operated during the control of the temperature. If the process temperature PV is lower than the lower tolerable deviation value LTV, the bypass is opened, and the first and second expansion means are closed. If the process temperature PV is equal to or higher than the lower tolerable deviation value LTV and is equal to or lower than the upper tolerable deviation value UTV, the bypass is opened, the first expansion means is opened and the second expansion means is closed so as to perform at least the operation with the small cooling power. When the time interval between the adjacent heat controlling signals exceeds the predetermined value, the second expansion means is additionally opened, and this operation with the large cooling power is performed for a period from elapsing of a period corresponding to the predetermined value to elapsing of the time interval.

These and other objects and features of the invention will become more apparent from the following description of preferred embodiments with reference to the accompanying drawings.

BRIEF DESCRIPTION OF THE DRAWINGS

FIG. 7 is a diagram illustrating conditions of heat controlling signals and others dependent on a current chamber temperature when a second method is implemented by an apparatus shown in FIG. 6; and FIG. 8 is a diagram illustrating conditions of heat controlling signals and others dependent on a current chamber temperature and other signals in a third method according to the invention.

DETAILED DESCRIPTION OF THE PREFERRED EMBODIMENTS

Figure 1:
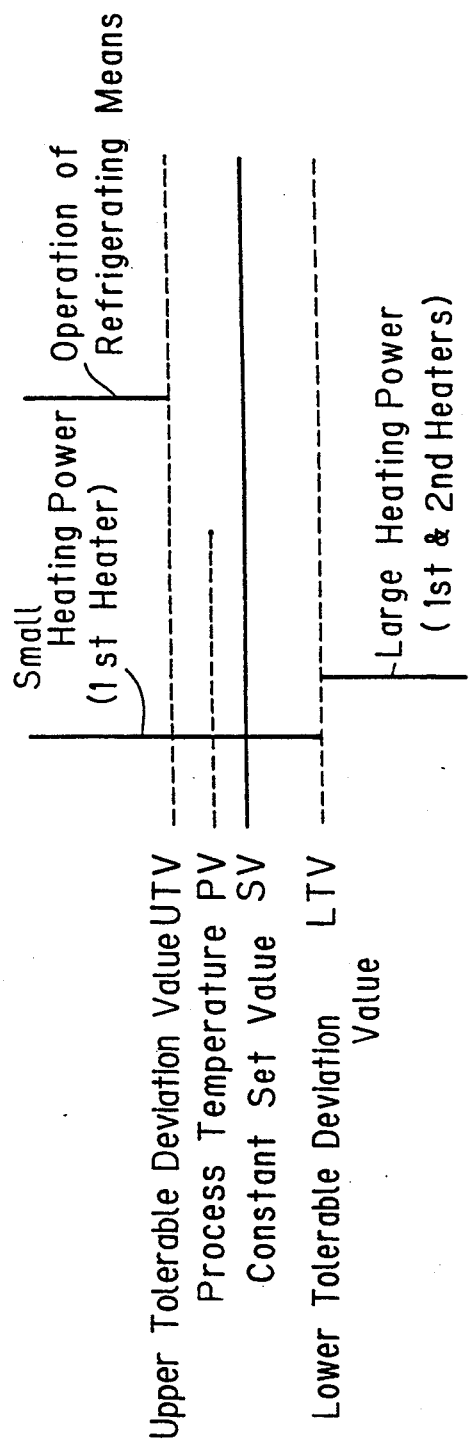
FIG. 1 is a diagram for illustrating a first method according to the invention.
Figure 2:
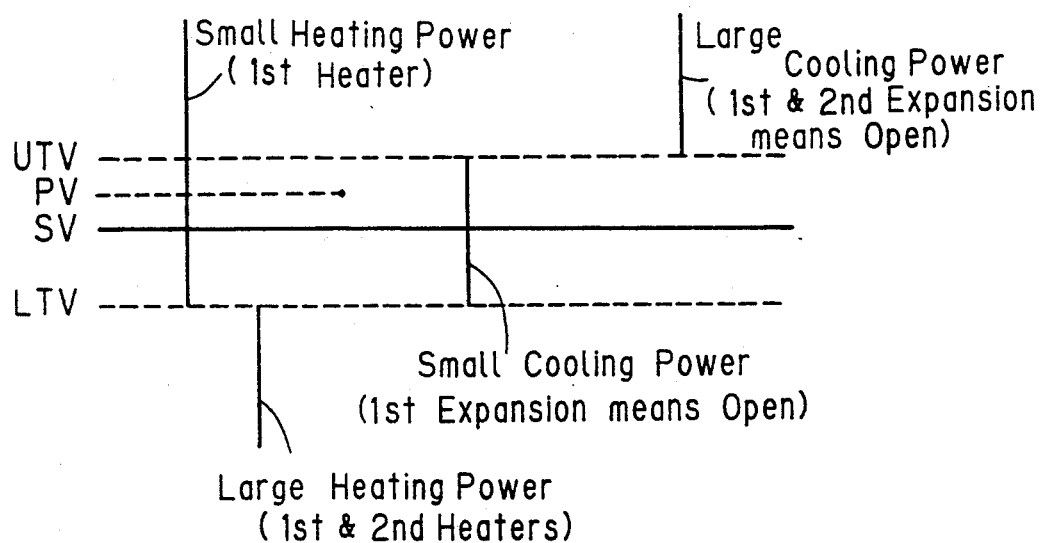
FIGS. 2 and 3 are diagrams for illustrating respective a second and third method according to the invention.
Figure 3:
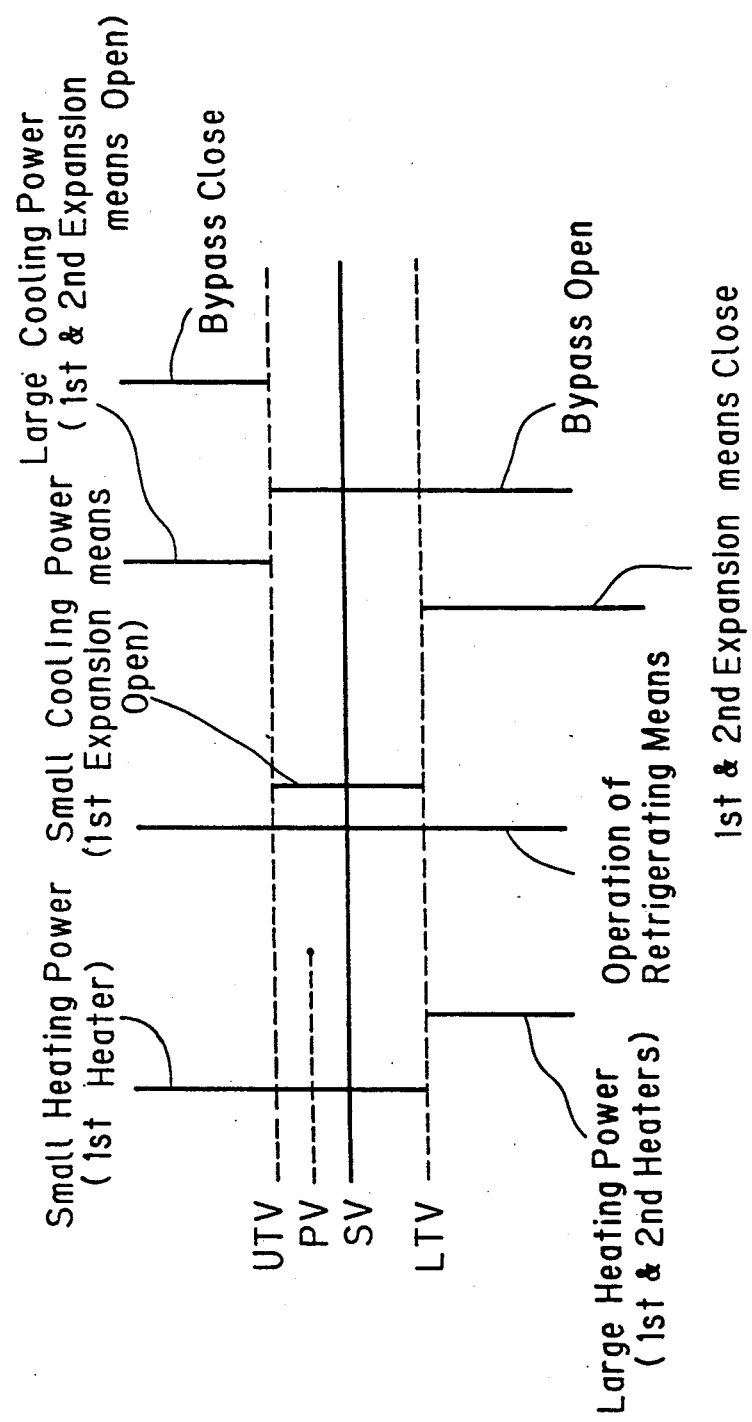
Figure 4:
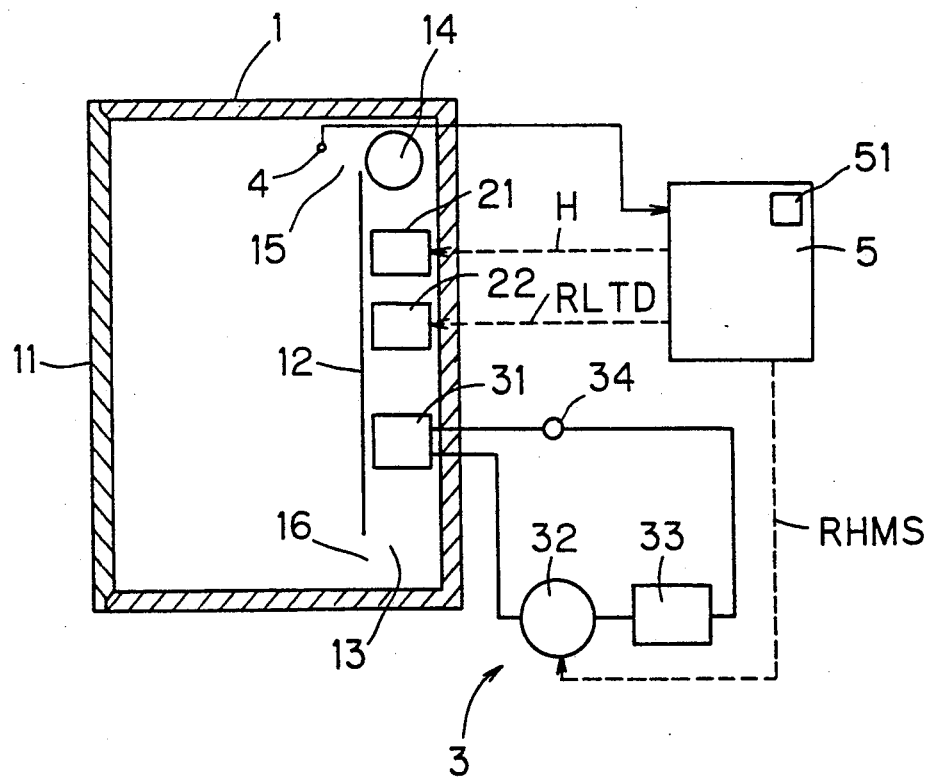
FIG. 4 is a schematic view of an apparatus for implementing a first method according to the invention.

FIG. 4 shows an example of an apparatus for implementing a first method according to the invention.

This apparatus is suitable to a case in which an intended set value SV of a temperature in a chamber is constant and is considerably higher than an environmental temperature, e.g., of 60° C. around the chamber.

This apparatus is a temperature equipment which is one type of an environmental testing equipment, and includes a temperature chamber 1 in which a constant temperature is to be maintained.

The temperature chamber 1 can be opened and closed by a door 11, and is provided at its rear or deep portion a partition 12 to form an air-conditioning room 13 behind the partition 12.

In the air-conditioning room 13, there are disposed a blower or fan 14, a first heater 21, a second heater 22, and a evaporator or cooler 31 of a refrigerator 3 in this order from the upper side. A temperature sensor 4 is disposed at an outlet 15 of the air-conditioning room 13 for detecting the process temperature (current temperature) PV in the chamber.

The fan 14 supplies the air of which temperature has been controlled in the air-conditioning room 13 through the outlet 15 into the chamber, and the air is introduced through an inlet 16 into the room 13 for circulation.

The refrigerator 3 is of a well-known type, and includes, in addition to the evaporator 31, a compressor 32, a condenser 33 and an expansion device 34. Various appropriate mechanisms such as capillary tubes and expansion valves may be employed as the device 34.

Outside the chamber, there is provided a temperature controller 5 to which the temperature sensor 4 always supplies signals representing the process temperature (currently detected temperatures) PV. This controller 5 is provided with a key board 51 for entering or presetting a constant set value SV of the chamber temperature to be maintained.

The controller 5 has a construction, in which the set value SV and the process temperature PV detected by the sensor 4 are compared for generating time-sharing proportional heat controlling signals H for operating the heater 21 based on a PID operation.

The controller 5 also has a construction, in which reversed LTD-signals RLTD for operating the heater 22 are generated when the process temperature PV is lower than the lower tolerable deviation value LTV which has been set with respect to the set value SV.

The controller 5 further includes a construction, in which heat monitor signals HMS are generated for inactivating the compressor 32 when a time interval t between the adjacent signals H, which increases in accordance with the increase of the process temperature PV, is not larger than a predetermined value of $\alpha$ seconds, and the reversed HMS-signals RHMS for activating the compressor 32 are generated for each period $(t-\alpha)$, when the time interval t exceeds the value of $\alpha$ second(s). The signal HMS rises simultaneously with the signal H, and lowers with a delay of $\alpha$ second(s) after lowering of the signal H. This predetermined delay time $\alpha$ is set so that a relationship of $(t-\alpha)>0$ may be established when the process temperature PV exceeds the upper tolerable deviation value UTV.

A first method of the invention carried out by this temperature equipment will be described below.

The set value SV is preset in the controller 5.

The sensor 4 continuously detects the process temperatures (current temperatures) PV and sends signals representative of the detected temperatures to the controller 5.

In the controller 5, the process temperatures PV detected by the sensor 4 and the set value SV are compared and the signals H are formed, based on the result of the PID operation which is performed based on the above comparison. Thus, the heater 21 is controlled to attain the set value SV based on the signals H.

Further, in the controller 5, the process temperatures PV from the sensor 4 and the lower tolerable deviation value LTV are compared, and, when the process temperature PV is lower than the lower tolerable deviation value LTV, the reversed LTD-signals RLTD are generated for operating the heater 22.

In this manner, when the process temperature PV is not lower than the lower tolerable deviation value LTV, the heater 21 is operated, based on the signals H (small heating power operation). When the process temperature PV is lower than the lower tolerable deviation value LTV, the heater 21 is operated, based on the signals H, and the heater 22 is also operated, based on the reversed LTD-signals RLTD (large heating power operation), so that the process temperature PV is rapidly increased toward the set value SV.

Conversely, when the process temperature PV is increased above the upper tolerable deviation value UTV, for example, by the heat from an article in the chamber 1, the controller 5 generates the reversed HMS-signals RHMS, by which the compressor 32 is operated to cool the chamber by the cooler 31. Thereby, the excessively increased chamber temperature can be rapidly lowered toward the set value SV.

Figure 5:
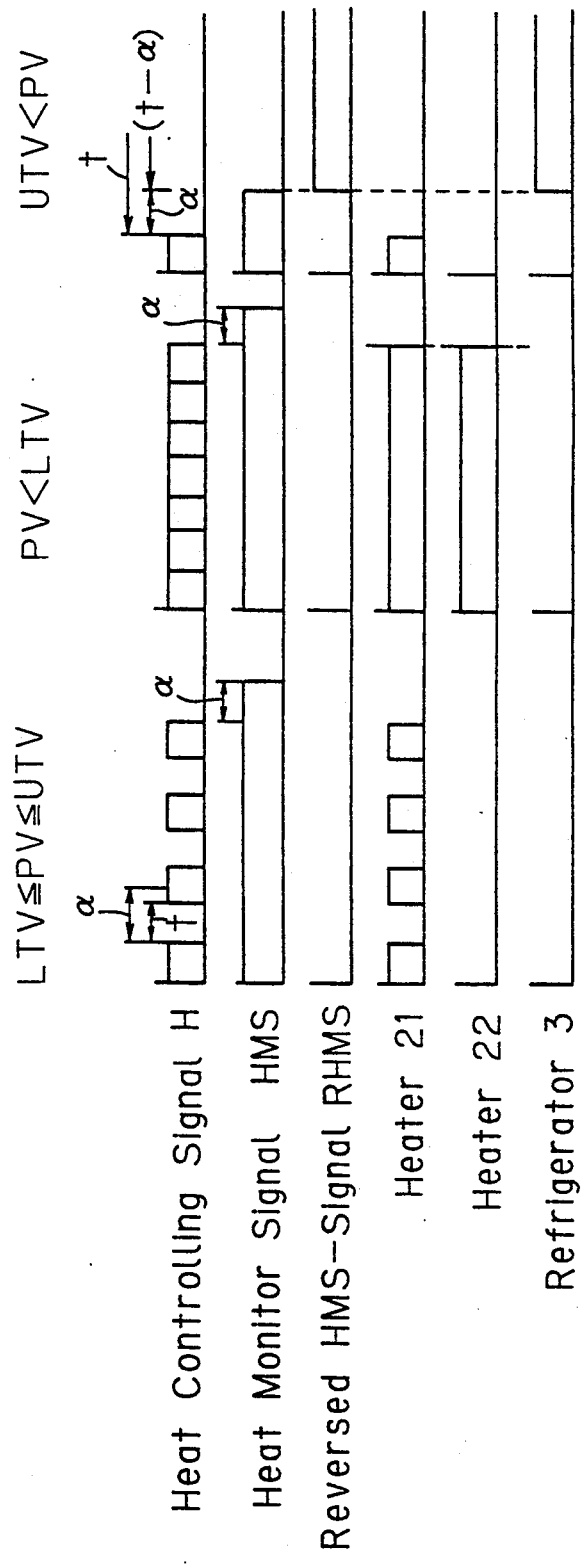
FIG. 5 is a diagram illustrating conditions of heat controlling signals and others dependent on a current chamber temperature when a first method is implemented by an apparatus shown in FIG. 4.

In the above control operation, there are such cases that (1) the process temperature PV is not lower than the lower tolerable deviation value LTV and is equal to or lower than the upper tolerable deviation value UTV, (2) the process temperature PV is lower than the lower tolerable deviation value LTV, and (3) the process temperature PV is higher than the upper tolerable deviation value UTV. FIG. 5 schematically shows generating conditions of the signals H, heat monitor signals HMS and reversed HMS-signals RHMS as well as operating conditions of the heaters 21 and 22 and refrigerator 3 in these three cases.

As can be seen in the Figure, the refrigerator 3 is operated in such a condition that the process temperature PV increases above the upper tolerable deviation value UTV, and thus the time interval t between the adjacent signals H exceeds the predetermined value of $\alpha$ second(s), so that the reversed HMS-signals RHMS are generated for a period of (t−$\alpha$).

Figure 6:
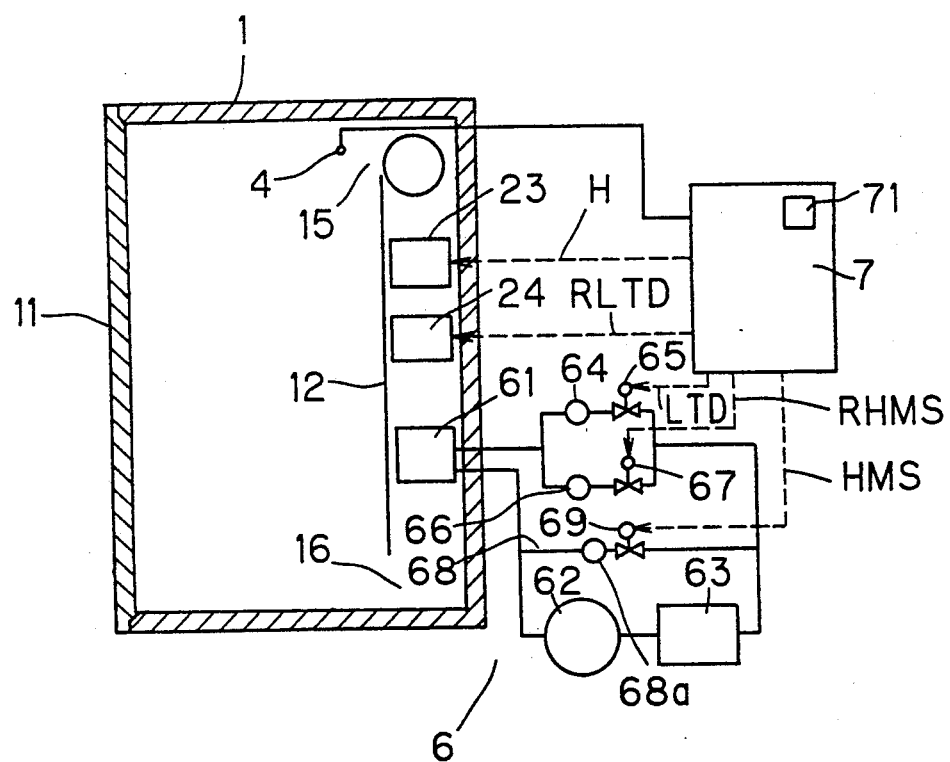
FIG. 6 is a schematic view of an apparatus for implementing second and third methods according to the invention.

FIG. 6 shows an example of an apparatus used for carrying out second and third methods according to the invention.

The apparatus in FIG. 6 is also a temperature equipment, and the same reference numbers are allotted to parts and members similar to those in FIG. 4.

In this temperature equipment, the heating means employs heaters 23 and 24, and the refrigerating means employs a refrigerator 6. A temperature controller 7 is disposed outside the chamber.

The refrigerator 6 includes a cooler 61 located in the chamber. The refrigerator 6 also includes a compressor 62, a condenser 63, a first expansion device 64, an electromagnetic valve 65 for selectively closing and opening the device 64, a second expansion device 66, an electromagnetic valve 67 for selectively closing and opening the device 66, a bypass 68 provided with an expansion device 68a and an electromagnetic valve 69 for selectively opening and closing the bypass 68, all of which are located outside the chamber. Various appropriate mechanisms such as capillary tubes and expansion valves may be employed as the expansion devices.

The temperature controller 7 continuously receives the process temperatures PV in the chamber from the temperature sensor 4. This controller 7 is provided with a key board 71 for presetting the constant set value SV of the chamber temperature or a time-dependent set value SVT which varies in accordance with the time.

The controller 7 has a construction, in which the set value SV or SVT and the process temperature PV detected by the sensor 4 are compared for generating time-sharing proportional heat controlling signals H for operating the first heater 23 based on a PID operation.

The controller 7 also has a construction in which reversed LTD-signals RLTD for operating the second heater 24 are generated when the process temperature PV is lower than the lower tolerable deviation value LTV which has been set with respect to the set value SV or SVT.

The controller 7 is also constructed to generate signals LTD for opening the first expansion device 64 when the process temperature PV is not lower than the lower tolerable deviation value LTV.

The controller 7 further includes a construction in which heat monitor signals HMS are generated for opening the refrigerator bypass 68 and closing the second expansion device 66 when the time interval t between the adjacent signals H, which increases in accordance with the increase of the process temperature PV, is not larger than a predetermined value of $\alpha$ second(s). In this construction, after the time interval t exceeds the value of $\alpha$ second(s), the reversed HMS-signals RHMS for rendering the bypass 68 closed and rendering the second expansion device 66 open are generated until the end of the period (t−$\alpha$). The signal HMS rises simultaneously with the signal H, and lowers with a delay of $\alpha$ second(s) after the lowering of the signal H. This predetermined delay time $\alpha$ is set so that, in a case of the constant set value SV, a relationship of (t−$\alpha$)>0 may be established when the process temperature PV exceeds the upper tolerable deviation value UTV, and that, in a case of the time-dependent set value SVT, it may allow sufficient follow of the chamber temperature to the time-dependent set value SVT while maintaining a relationship of (t−$\alpha$)>0.

A second method of the invention carried out by this temperature equipment will be described below.

In this method, the compressor 62 of the refrigerator 6 is continuously operated during the control of the temperature.

The set value SV is preset in the controller 7.

The sensor 4 continuously detects the process temperatures PV and sends signals representative of the detected temperature to the controller 7.

In the controller 7, the process temperatures PV detected by the sensor 4 and the set value SV are compared and the signals H are formed, based on the result of the PID operation which is performed based on the above comparison. Thus, the heater 23 is controlled to operate to attain the set value SV based on the signals H.

Further, in the controller 7, the process temperatures PV from the sensor 4 and the lower tolerable deviation value LTV are compared, and, when the process temperature PV is lower than the lower tolerable deviation value LTV, the reversed LTD-signals RLTD are generated for operating the heater 24.

In this manner, when the process temperature PV is not lower than the lower tolerable deviation value LTV, the heater 23 is operated, based on the signals H (small heating power operation). When the process temperature PV is lower than the lower tolerable deviation value LTV, the heater 23 is operated, based on the signals H, and the heater 24 is also operated, based on the reversed LTD-signals RLTD (large heating power operation), so that the process temperature PV is rapidly increased toward the set value SV.

In the refrigerator 6, when the process temperature PV is lower than the lower tolerable deviation value LTV, the electromagnetic valve 69 is opened for opening the bypass 68, based on the generated heat monitor signals HMS. Meanwhile, the electromagnetic valves 65 and 67 for the first and second expansion devices 64 and 66 are closed.

When the process temperature PV increases to or above the lower tolerable deviation value LTV, the signals LTD cause the electromagnetic valve 65 for the first expansion device 64 to open without closing the bypass. This achieves the operation with the small cooling power.

When the process temperature PV is increased above the upper tolerable deviation value UTV, for example, by the heat from an article in the chamber 1, the controller 7 generates the reversed HMS-signals RHMS, by which the electromagnetic valve 67 is opened so as to open the second expansion device 66 and the electromagnetic valve 69 is closed for closing the bypass 68, whereby the operation with the large cooling power is carried out. Thereby, the excessively increased chamber temperature can be rapidly lowered toward the set value SV.

In the above control operation, there are such cases that (1) the process temperature PV is not lower than the lower tolerable deviation value LTV and is equal to or lower than the upper tolerable deviation value UTV, (2) the process temperature PV is lower than the lower tolerable deviation value LTV, and (3) the process temperature PV is higher than the upper tolerable deviation value UTV. FIG. 7 schematically shows generating conditions of the signals H, heat monitor signals HMS, reversed HMS-signals RHMS, reversed LTD-signals RLTD and signals LTD as well as conditions of the heaters 23 and 24, first and second expansion devices 64 and 66, and the bypass 68 in these three cases.

A third method of the invention carried out by this temperature equipment shown in FIG. 6 will be described below.

Also in this method, the compressor 62 of the refrigerator 6 is continuously operated during the control of the temperature.

The time-dependent set value SVT is preset in the controller 7.

The sensor 4 continuously detects the process temperature PV and send signals representative of the detected temperature to the controller 7.

In the controller 7, the process temperature PV detected by the sensor 4 and the set value SVT are compared and the signals H are formed, based on the result of the PID operation which is performed based on the above comparison. Thus, the heater 23 is controlled to attain the set value SVT based on the signals H.

Further, in the controller 7, the process temperatures PV from the sensor 4 and the lower tolerable deviation value LTV are compared, and, when the process temperature PV is lower than the lower tolerable deviation value LTV, the reversed LTD-signals RLTD are generated for operating the heater 24.

In this manner, when the process temperature PV is not lower than the lower tolerable deviation value LTV, the heater 23 is operated, based on the signals H (small heating power operation). When the process temperature PV is lower than the lower tolerable deviation value LTV, the heater 23 is operated, based on the signals H, and the heater 24 is also operated, based on the reversed LTD-signals RLTD (large heating power operation), so that the process temperature PV is rapidly increased toward the set value SV.

In the refrigerator 6, when the process temperature PV is lower than the lower tolerable deviation value LTV, the electromagnetic valve 69 is opened for opening the bypass 68, based on the generated heat monitor signals HMS. Meanwhile, the electromagnetic valves 65 and 67 for the first and second expansion devices 64 and 66 are closed.

When the process temperature PV increases to or above the lower tolerable deviation value LTV, the signals LTD cause the electromagnetic valve 65 for opening the first expansion device 64 to open without closing the bypass.

When the time interval t between the heat controlling signals H exceeds the predetermined value of α due to a rapid change of the set value SVT or others, the controller 7 generates the reversed HMS-signals RHMS, whereby the electromagnetic valve 67 is opened so as to open the second expansion device 66 and the electromagnetic valve 69 is closed so as to close the bypass 68, and thus the operation is performed with the large cooling power.

The operations with the large heating power and the large cooling power described above allow the process temperature PV to sufficiently follow the set value SVT even in a case of rapid change of the set value SVT, which is impossible by the mere PID control.

FIG. 8 schematically shows output conditions of the heat monitor signals HMS for rendering the bypass open and the heat controlling signals H in the temperature control operation for the time-dependent set value SVT as well as the conditions of the operations with the large heating power and the large cooling power.

According to the first and second methods of the invention, as described hereinabove, the temperature in the chamber is controlled to be the constant set value in such a manner that, when the current chamber temperature lowers below the lower tolerable deviation value, the chamber temperature can be rapidly raised, and when the chamber temperature is raised above the upper tolerable deviation value, for example, due to the heat from the article in the chamber, the chamber temperature can be rapidly lowered, whereby the chamber temperature can be maintained at or near the set value.

According to the third method of the invention, the chamber temperature is controlled toward the time-dependent set value by sufficiently following the chamber temperature to the time-dependent set value.

Although particular preferred embodiment of the invention have been disclosed in detail for illustrative purpose, it will be recognized that other variations or modifications may be made without departing from the spirit and scope of the invention as claimed.

What is claimed is:

1. A temperature control method for controlling a temperature in a chamber to a set value, said method comprising:

providing heating means which can select large and small heating powers for heating said chamber and refrigerating means for cooling said chamber;

detecting a current temperature in said chamber;

operating said heating means with a small heating power when a detected temperature is equal to or higher than a lower tolerable deviation value predetermined with respect to said set value of said chamber temperature, and operating said heating means with a large heating power when said detected temperature is lower than said lower tolerable deviation value;

operating said heating means based on time-sharing proportional heat controlling signals at least during the operation of said heating means with said small heating power;

generating a signal which indicates a relationship that a time interval between adjacent signals of said heat controlling signals is larger than a predetermined time interval while maintaining said relationship; and operating said refrigerating means based on signal indicating said relationship at least when said signal indicating said relationship is generated;

wherein said refrigerating means operating step comprises operating said refrigeration means at large and small cooling powers, wherein operating said refrigerating means with said large cooling power is based on a signal used for a large cooling power operation and formed of said signal, which indicates said relationship for the operation of said refrigerating means and is generated when said time interval between adjacent said heat controlling signals is larger than said predetermined time interval while said relationship is maintained, and wherein operating said refrigerating means with said small cooling power is when said time interval between adjacent said heat controlling signals is equal to or smaller than said predetermined time interval, and said detected temperature is equal to or higher than a lower tolerable deviation value predetermined with respect to said set value of said chamber temperature; and wherein said refrigerating means operating step includes operating first and second expansion means so that said first expansion means is opened and said second expansion means is closed so as to obtain said small cooling power and both the first and second expansion means are opened so as to obtain said large cooling power;

the temperature control method further comprising providing a closable bypass connecting a condenser and a compressor of said refrigerating means together, and continuously operating said compressor during the temperature control, and closing said first and second expansion means and opening said bypass when said detected temperature is lower than said lower tolerable deviation value, wherein said first expansion means is opened and said second expansion means is closed so as to obtain said small cooling power while said bypass is maintained open, and said first and second expansion means are opened and said bypass is closed so at to obtain said large cooling power.

2. A temperature control method as claimed in claim 1, wherein said heating means operating step comprises operating first and second heaters wherein said small heating power may be obtained by operating said first heater and said large heating power may be obtained by operating both said first and second heaters.

3. A temperature control method as claimed in claims 1 or 2, wherein said set value is a constant set value.

4. A temperature control method as claimed in claims 1 or 2, wherein said set value is a time-dependent variable set value.

* * * * *